(12) United States Patent
Sugita et al.

(10) Patent No.: US 8,530,412 B2
(45) Date of Patent: Sep. 10, 2013

(54) EJECTION LIQUID, EJECTION METHOD, METHOD OF MAKING DROPLETS FROM LIQUID, CARTRIDGE AND EJECTION DEVICE

(75) Inventors: Masaru Sugita, Tokyo (JP); Yohei Masada, Kawasaki (JP); Hideki Kaneko, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/987,016

(22) Filed: Jan. 7, 2011

(65) Prior Publication Data

US 2011/0104113 A1    May 5, 2011

Related U.S. Application Data

(62) Division of application No. 11/908,600, filed as application No. PCT/JP2006/307019 on Mar. 28, 2006, now abandoned.

(30) Foreign Application Priority Data

Mar. 30, 2005   (JP) ................................. 2005-098749

(51) Int. Cl.
*A61K 38/28*   (2006.01)
*A61K 31/205*  (2006.01)
*B41J 2/01*    (2006.01)
*C08K 5/151*   (2006.01)

(52) U.S. Cl.
USPC ............... 514/5.9; 514/556; 530/303; 347/1; 524/753

(58) Field of Classification Search
None
See application file for complete search history.

(56) References Cited

U.S. PATENT DOCUMENTS

| | | | |
|---|---|---|---|
| 4,654,207 A | 3/1987 | Preston | |
| 5,451,251 A * | 9/1995 | Mafune et al. | 106/31.48 |
| 5,894,841 A | 4/1999 | Voges | |
| 6,234,167 B1 | 5/2001 | Cox et al. | |
| 6,328,728 B1 | 12/2001 | Holladay et al. | |
| 6,926,392 B2 | 8/2005 | Sasaki et al. | |
| 7,344,236 B2 | 3/2008 | Morimoto | |
| 7,585,641 B2 | 9/2009 | Bandla et al. | |
| 7,594,507 B2 | 9/2009 | Davis | |
| 7,659,987 B2 | 2/2010 | Utsunomiya et al. | |
| 2002/0142341 A1 | 10/2002 | Kameyama et al. | |
| 2002/0177221 A1 | 11/2002 | Nishiguchi et al. | |
| 2003/0064052 A1 | 4/2003 | Waters et al. | |
| 2004/0042972 A1 | 3/2004 | Truong-Le et al. | |
| 2005/0261258 A1* | 11/2005 | Kolodney et al. | 514/169 |
| 2007/0248571 A1 | 10/2007 | Masada et al. | |
| 2009/0053174 A1 | 2/2009 | Kaneko et al. | |

FOREIGN PATENT DOCUMENTS

| | | |
|---|---|---|
| CN | 1464791 A | 12/2003 |
| CN | 1593917 A | 3/2005 |
| GB | 1 563 311 A | 3/1980 |
| JP | 2002-248171 | 9/2002 |
| JP | 2002-355025 | 12/2002 |
| JP | 2003-154655 | 5/2003 |
| JP | 2006-36725 A | 2/2006 |
| JP | 2006117634 A | 5/2006 |
| WO | 01/01960 A1 | 11/2001 |
| WO | 02/094342 | 11/2002 |
| WO | 03/086443 | 10/2003 |
| WO | 2006/035923 | 4/2006 |
| WO | 2006/035977 | 4/2006 |

OTHER PUBLICATIONS

Goodall et al. Aerosolization of protein solutions using thermal inkjet technology. J Aerosol Med. 2002 Fall;15(3):351-7.*
Roda et al. Protein microdeposition using a conventional ink-jet printer. Biotechniques. Mar. 2000;28(3):492-6.*
Official Action dated May 20, 2011 in Chinese Application No. 200680010855.6.
Leonardo R. Allain, et al., "Microarray sampling-platform fabrication using bubble-jet technology for a biochip system", Fresenius J. Anal. Chem., vol. 371, 2001, pp. 146-150.
E. I. Howard, et al., "Ink-Jet Printer Heads for Ultra-Small-Drop Protein Crystallography", BioTechniques, vol. 33, No. 6, Dec. 2002, pp. 1302-1306.
Registry Database Entry for Laurylbetaine, RN 683-10-3, Nov. 16, 1984 [online]. [retrieved on 10105/2010]. Retrieved from: Registry database, STN International, Columbus, Ohio, USA.
Aungst, et al., "Comparison of the effects of various transmucosal absorption promoters on buccal insulin delivery", International Journal of Pharmaceutics, vol. 53, 1989, pp. 227-235.
United States National Library of Medicine, ChemIDplus Advanced entry for Lauramidopropyl betaine [online], [retrieved on Feb. 26, 2010]. Retrieved from the Internet: <URL:http://chem.sis.nlm.nih.gov/chemidplus/ProxyServlet?objectHandle=DBMaint&actionHandle=default&nextPage=jsp/chemidheavy/ResultScreen.jsp&ROW_NUM=0&TXTSUPERLISTID=004292108>.
United States National Library of Medicine, ChemIDplus Advanced entry for Polysorbate 20 [online], [retrieved on Feb. 26, 2010]. Retrieved from the Internet: <URL:http://chem.sis.n1m.nih.gov/chemidplus/ProxyServlet?objectHandle=Search&actionHandle=getAII3DMViewFiles&nextPage=jsp%2Fcommon%2FChemFull.jsp%3FcalledFrom%3D&chemid=009005645&formatType=_3D>.

(Continued)

*Primary Examiner* — David Romeo
(74) *Attorney, Agent, or Firm* — Fitzpatrick, Cella, Harper and Scinto

(57) ABSTRACT

The present invention provides a liquid composition, as an ejection liquid used for stably ejecting liquid droplets, including at least one kind of a protein and a peptide, and a compound having a betaine skeleton by application of thermal energy to the liquid; a method of making droplets form the liquid; and an ejection method and an ejection device suitable for utilizing protein liquid droplets. By adding a compound having a betaine skeleton to an aqueous solution of at least one kind of a protein and a peptide, the liquid composition is improved in stability for ejection by application of thermal energy. Further, a surfactant may be further added to the liquid composition containing the compound having a betaine skeleton, and in this case the effect of stable ejection can be obtained.

2 Claims, 4 Drawing Sheets

(56) References Cited

OTHER PUBLICATIONS

United States National Library of Medicine,ChemIDplusAdvancedentry for Lauryldimethylbetaine [online],[retrieved on Feb. 26, 2010]. Retrieved from the Internet: <URL:http://chem.sis.n1m.nih.gov/chemidplus/ProxyServlet?objectHandle=Search&actionHandle=getAII3DMViewFiles&nextPage=jsp%2Fcommon%2FChemFull.jsp%3FcalledFrom%3D& chemid=000683103&formatType_3D>.

European Search Report dated Mar. 7, 2012 in European Application No. 06730967.4.

Santoro, et al., "Increased Thermal Stability of Proteins in the Presence of Naturally Occurring Osmolytes", Biochemistry, vol. 31, No. 23, 1992, pp. 5278-5283.

\* cited by examiner

EJECTION LIQUID, EJECTION METHOD, METHOD OF MAKING DROPLETS FROM LIQUID, CARTRIDGE AND EJECTION DEVICE

This application is a divisional of Application Ser. No. 11/908,600, which was the National Stage of International Application No. PCT/JP2006/307019, filed Mar. 28, 2006. The contents of each of the foregoing applications is incorporated herein by reference.

TECHNICAL FIELD

The present invention relates to a liquid composition containing at least one kind of a protein and a peptide suitable for making droplets form the liquid composition, to a method of making droplets form the liquid composition, and to an ejection device using the method of making droplets form the liquid composition.

BACKGROUND ART

In these years, many attempts of using a protein solution as droplets have been made. Examples of such attempts include a transmucosal administration as a drug delivery method, and applications to a biochip or a biosensor because they need only a trace amount of protein. In addition, a method of using protein liquid microdroplets has also attracted attention in the field of screening a bioactive substance (Japanese Patent Application Laid-Open No. 2002-355025; Allain L R, et al., "Fresenius J. Anal. Chem." 2001, Vol. 371, p. 146-150; and Howard E I, Cachau R E "Biotechniques" 2002, Vol. 33, p. 1302-1306).

Recently, protein, particularly, enzyme or useful protein having bioactivity is going to be able to be mass-produced through a gene-recombination technique so that liquid droplets formation of protein can become a useful means for the search and application of protein as new medicine, and the applicable field. Above all, the means of administering various drugs to a patient with the use of the liquid fine droplet has become more important, particularly in the respect of administering protein, peptide and other biological substances through a lung. Lungs have alveoli with a surface area as large as 50 to 140 $m^2$, have epithelium which is an absorption barrier as extremely thin as 0.1 µm, in addition, have enzymatic activity lower than that of the alimentary canal, and accordingly have received attention as a substituting administration route for the injection of a high-molecule-peptide-based drug represented by insulin.

In general, it is known that the intrapulmonary deposition of a liquid fine droplet of a drug largely depends on an aerodynamic particle size thereof, and above all, in order to deliver the droplet to the alveoli, deep parts of the lung, it is indispensable to develop an administration form capable of administering droplets having particle sizes of 1 to 5 µm and the narrow distribution of the particle sizes with high reproducibility and stable formulation.

There have been conventionally some methods of administering a formulation to the interior of the body particularly to a perimeter of a respiratory organ, so that these methods will be now explained with examples. There is a metered-dose inhaler (MDI) of aerosolizing the formulation in a suspensoid aerosol form enables quantitative atomisation, by employing a liquefied incombustible or flame-resistant gas as a pressure carrier, and controlling a unit volume of the liquefied gas to be ejected at a single time. However, the inhaler has a problem that the size of a droplet in the above-described range is not sufficiently controlled, and besides, the pressure carrier may not be good for health. There is also a spraying method used for atomising a liquid formulation, which employs water and ethanol as a medium, and converts the liquid formulation to microdroplets by ejecting it together with a gas under pressure for transportation through a capillary. Accordingly, it is theoretically possible for the atomising method to control a atomised amount by specifying a fluid volume of the liquid formulation supplied into such a capillary flow path, but is difficult to control the diameter of the droplet.

Particularly, a spray type of atomisation uses a gas under pressure which has been used in a process for making microdroplets from liquid, subsequently as a gas for transporting the atomised microdroplets in a flow. For this reason, it is structurally difficult to vary a quantity (density) of the microdroplets floating in airflow for transportation according to a purpose.

As a method of producing the above-described droplets with a narrow particle size distribution, there is a report on the use of a droplet-generating device which forms extremely microdroplets based on a sort of principle used in an ink jet printing (for instance, U.S. Pat. No. 5,894,841 and Japanese Patent Application Laid-Open No. 2002-248171). Here, such ink jet system will be described. The system consists of the procedure of introducing a liquid to be ejected into a small chamber, applying pushing force to the liquid, and ejecting the droplets through an orifice. A usable pushing method includes, for instance, a method of forming bubbles for ejecting the droplets through the orifice on the chamber with the use of an electro-thermal converter such as a thin film resistor (thermal ink jet system), and a method of directly pushing a liquid through the orifice on the chamber with the use of a piezooscillator (piezo ink jet system). The chamber and the orifice are built in a print head element, and the print head element is connected to a supply source for a liquid and also to a controller for controlling the ejection of the droplets.

When making a drug absorbed from lungs, it is necessary to precisely control the dosage particularly for the above-described protein formulation, so that liquid droplet formation based on the principle of the ink jet system is a very preferable form, because it can control an ejection rate. In addition, though a liquid is required to be reliably ejected, a protein solution having only adjusted surface tension and viscosity is ejected unstably, so that there was a case where the protein solution is hardly ejected with a high degree of reproducibility and efficiency.

The liquid droplet formation of the above-described protein and peptide on the basis of a principle of the ink jet system has a problem that the protein has a frail spatial configuration and therefore may cause the aggregation and decomposition of the protein when the configuration has been destroyed. When the liquid droplets are formed based on the principle of the ink jet system, physical force such as pressure and shear force are applied to the liquid droplets, and each liquid fine droplet has its peculiar high surface energy. They make the configuration of most of proteins unstable (When the thermal ink jet system is employed, heat is added thereto in addition to them). The liquid droplet formation particularly on the basis of the principle of the ink jet system has the problem that storage in a long period is unstable, and further that the above-described physical force is extremely higher than the shear force and thermal energy applied in normal stirring and heat treatment. (It is considered that, for instance, the instantaneous load of 90 atmospheres at 300° C. is applied to the liquid droplets in the thermal ink jet system). In addition, a plurality of physical forces are simultaneously applied to the liquid droplets. For this reason, protein tends to become much more unstable than in a process of normally treating protein, so that there has been a case where a conventionally-used technology of stabilizing the protein is insufficient. Once the problem happens, proteins aggregate while the droplets are formed, which causes clogging in a nozzle and makes the droplets hardly ejected.

Furthermore, a size of a droplet suitable for lung inhalation is 1 to 5 µm, which is very smaller than a droplet of about 16 µm used in a currently commercially available printer, and results in applying larger surface energy and shear force onto the droplet. For this reason, it is extremely difficult to eject protein as microdroplets suitable for the lung inhalation.

In consideration of the above-described various uses, a method of ejecting a protein solution is preferably based on the principle of a thermal ink jet system, because it has a low manufacturing cost and can increase the density of nozzles.

On the other hand, a method of adding a water-soluble polymer or albumin, such as a surfactant, glycerol, various saccharides and polyethylene glycol, which are known as the method of stabilizing protein, has little or no effect of improving ejecting performance when ejecting protein with a thermal ink jet system.

In regard to a liquid composition of droplets to be inhaled into lungs, which are formed with the use of a thermal ink jet system, there is disclosed a method of adding a compound for adjusting surface tension and/or a moisturizing agent to a protein solution (for instance, the pamphlet of International Publication No. WO02/094342). The above method includes adding a water-soluble polymer such as a surfactant and polyethylene glycol to a protein solution, because describing that the water-soluble polymer improves the stability of protein in a solution of a formed liquid droplet, through decreasing surface tension and viscosity of the solution, and keeping the moisture of the solution.

However, the pamphlet does not describe the stability of ejection, furthermore, the addition of a surfactant and a water-soluble polymer shows the insufficient effect when the concentration of protein and peptide is high, and there was a case where an additive in itself aggravated the stability of the ejection. In addition, many surfactants do not have an effect on the stability of the ejection at all, and in other words, surface tension, viscosity or a moisture retention effect does not control the stability of the ejection. To put it differently, the above-described method was not a general one for stabilizing the ejection when ejecting protein and peptide with a thermal ink jet system.

As described above, an ink jet technology is well known as a method of making liquid fine droplets from a liquid sample and ejecting them, and particularly has a feature of showing high controllability for even a trace amount of a liquid to be ejected after having converted into liquid droplets. The fine-droplet-ejecting type of an ink jet system includes an oscillation type using a piezoelectric element and a thermal ink jet system using a micro-heater element. The oscillation type using the piezoelectric element has limitation in miniaturization for the piezoelectric element to be used, and accordingly in the number of installed ejection orifices per unit area. In addition, a necessary cost for producing an ejection device sharply increases with the increase of the number of arranged ejection orifices per unit area. In contrast to this, the thermal ink jet system can comparatively easily miniaturize the micro-heater elements to be used in the ejection device, can increase the number of the arranged ejection orifices per unit area in comparison with the oscillation type system using the piezoelectric element, and can far reduce a necessary production cost for the ejection device.

When applying a thermal ink jet system to liquid droplet formation, it is necessary to adjust a physical property of a liquid to be ejected, so as to control an appropriate atomisation state and a liquid volume of a liquid fine droplet to be ejected from each ejection orifice. Specifically, a liquid composition such as a type of a solvent, a composition and a concentration of a solute, which composes a liquid sample to be ejected is well adjusted so as to provide a target liquid volume of a liquid fine droplet.

Furthermore, various technological developments are being proceeded also on a droplet-ejecting mechanism based on the principle of a thermal ink jet system. While a conventional ink jet printer head ejects liquid droplets having the individual liquid volume of about several picoliters, an ejecting technology and an ejecting mechanism which have been developed recently forms an extremely liquid fine droplet of a subpicoliter or femtoliter order (see, for instance, Japanese Patent Application Laid-Open No. 2003-154655).

DISCLOSURE OF THE INVENTION

An object of the present invention is to provide a liquid composition as an ejection liquid used for stably ejecting liquid droplets containing at least one kind of a protein and a peptide by application of thermal energy to the liquid, and to provide an ejection method and an ejection device suitable for utilization of protein liquid droplets.

The ejection liquid of the present invention is characterized by including one kind selected from a protein and a peptide, a compound having a betaine skeleton, and a liquid medium.

The ejection method of the present invention is characterized in that liquid droplets are made from the above-described ejection liquid based on the principle of the thermal ink jet system, and the liquid droplets are ejected.

The cartridge for ejecting a liquid according to the present invention is characterized by comprising a tank for accommodating the above-described ejection liquid, and an ejection head based on the thermal ink jet principle.

The liquid inhalation device of the present invention is characterized by comprising the above-described cartridge, and a flow path part and opening part for guiding a liquid to be ejected, from a liquid ejection part of an ejection head of the cartridge based on the thermal ink jet principle, to an inhaling site of a user.

The method of making liquid droplets from a liquid according to the present invention is characterized in that the method makes liquid droplets from a liquid containing at least one kind of a protein and a peptide by applying thermal energy to the liquid, wherein the above-described liquid includes a compound having a betaine skeleton.

According to the present invention, an ejection liquid which can be stably ejected after thermal energy has been applied thereto can be provided, by adding a compound having a betaine skeleton to a solution containing at least one kind of a protein and a peptide. In addition, it is further possible to eject a protein solution with a higher concentration by further adding a surfactant to the ejection liquid, because the addition provides a synergistic effect of stabilizing ejection. When at least one kind of a protein and a peptide is a pharmaceutically effective ingredient, at least one kind of the protein and peptide of the pharmaceutically effective ingredient arrives at a lung by ejecting the ejection liquid from a portable ejection device to convert it into liquid droplets, and inhaling the droplet, and the pharmaceutically effective ingredient can be absorbed by the lung. The above-described method can be also used for the preparation of a biochip or a biosensor, sensing, and screening for a biological substance, by ejecting at least one kind of the protein and peptide onto a substrate with the method.

Other features and advantages of the present invention will be apparent from the following description taken in conjunction with the accompanying drawings, in which like reference characters designate the same or similar parts throughout the figures thereof.

BEST MODE FOR CARRYING OUT THE INVENTION

Figure 1:
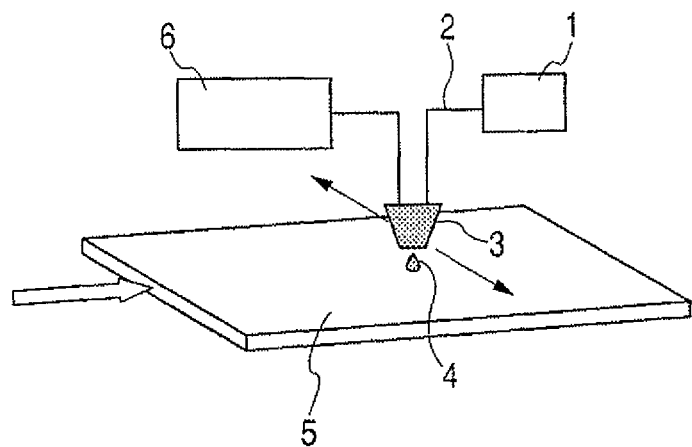
FIG. 1 is a diagrammatic view for explaining a method for ejecting protein onto a substrate.

Preferred embodiments of the present invention will now be described in detail in accordance with the accompanying drawings.

An object of the present invention is to provide a liquid composition for an ejection liquid used for stably ejecting liquid droplets containing at least one kind of a protein and a peptide by applying thermal energy to it, to provide an ejection method suitable for the use of the liquid droplet containing protein, and to provide an ejection device therefor.

The present invention will be now described in detail below.

The protein used in the present invention means an arbitrary polypeptide which consists of amino acids bonded with each other by a peptide bond, and can be dissolved or dispersed in an aqueous solution. In addition, the peptide used in the present invention means a compound which consists of two or more and 100 or less amino acids bonded with each other through a peptide bond. Protein and peptide may be chemically synthesized or refined from a natural source, but typically, are native protein and a recombinant of peptide. Protein and peptide can be also chemically reformed by covalently bonding polyethylene glycol with an amino acid residue in the molecule of protein and peptide or the like, to enhance an effect of prolonging a therapeutic effect of protein and peptide and the like.

When implementing the present invention, a liquid to be used can contain various protein and peptide of which the liquid droplet is desired to be formed. Most typically, the purpose of making the liquid droplet from the liquid containing protein and peptide of the present invention is to deliver useful protein and peptide for medical treatment to a lung. These examples include various hematopoietic factors such as calcitonin, a blood coagulation factor, ciclosporin, G-CSF, GM-CSF, SCF, EPO, GM-MSF and CSF-1; interleukin such as IL-1, IL-2, IL-3, IL-4, IL-5, IL-6, IL-7, IL-8, IL-9, IL-10, IL-11 and IL-12; an IGF; and cytokine including M-CSF, thymosin, TNF and LIF. Usable protein having another therapeutic effect includes vasoactivity peptide; interferon (alpha, beta, gamma or common interferon); a growth factor or a hormone, such as a human growth hormone and another animal growth hormone (like growth factors of bovine, pig or chicken); insulin; oxytocin; angiotensin; methionine enkephalin; substance P; ET-1; FGF; KGF; EGF; IGF; PDGF; LHRH; GHRH; FSH; DDAVP; PTH; vasopressin; glucagon; and somatostatin. A protease inhibitor such as leupeptin and pepstatin, and a metalloproteinase inhibitor (such as TIMP-1, TIMP-2 and other proteinase inhibitors) are also used. A nerve growth factor such as BDNF and NT3 is also used. A plasminogen activator such as tPA, urokinase and streptokinase is also used. A peptide part of protein having a main structure or one part of parent protein and at least one part of various biological properties of parent protein is also used. An analog such as a substitution or defect analog, modified amino acid such as a peptide analog, or a compound including the above-described substance modified with a water-soluble polymer such as PEG and PVA is also used. It has been clear in Critical Reviews in Therapeutic Drug Carrier Systems, 12 (2&3) (1995) that the above-described protein can be delivered to a lung.

Furthermore, in a field of the preparation of a biochip and a biosensor, the screening of protein and peptide and the like, the following many substances in addition to the above-described protein and peptide can be also used: various enzymes such as oxidase, reductase, transferase, hydorase, lyase, isomerase, synthetase, epimerase, mutase and racemase; various antibodies and receptors such as IgG and IgE; protein and peptide used for diagnosis, such as antigen of them, allergen, chaperonin, avidin and biotin; and the above-described substances modified with a reagent for immobilization.

Usable protein and peptide contained in the above-described ejection liquid has a molecular weight, for instance, in a range of 0.5 kDa to 150 kDa. In addition, a content of at least one kind selected from protein and peptide is determined in accordance with a purpose and application thereof, and is preferably determined in a range of 1 ng/ml to 200 mg/ml.

It is preferable that a liquid medium contains mainly water, and that a ratio of water to the medium is 50% or higher. In addition to water which is a main component of the medium, a water-soluble organic solvent and an auxiliary such as alcohol can be added as the medium.

It is generally known to add a surfactant and a solvent such as ethylene glycol, in order to improve ejection properties of ink to which thermal energy is applied. However, when ejecting a protein and peptide solution, the ejection properties were not perceptibly improved by adding only them, so that a new additive was necessary.

As a result of conducting extensive studies, the present inventors found that a solution containing a compound having a betaine skeleton in a protein and peptide is suitable for forming a stable liquid droplet even when thermal energy has been applied.

As a method for applying the above-described thermal energy to liquid droplets and ejecting them, there are, for instance, a method of heating a tube and ejecting a liquid inside it from an opening, which is disclosed in U.S. Pat. No. 6,234,167, and a method based on the principle of the thermal ink jet method. The thermal ink jet system is the method of applying the thermal energy to the liquid with a heater, heating and bubbling the liquid with the energy, and ejecting the liquid droplet from the opening of an end of a liquid-existing space; and has a feature of uniformly ejecting the highly accurate number of liquid droplets in comparison with the above-described method of heating the tube, by separating the heaters into fine many parts.

Hereafter, a configuration based on the principle of the thermal ink jet method is mainly described because the thermal ink jet method most conspicuously shows an improved effect for ejection properties, but the piezoelectric ink jet method of ejecting a liquid in a nozzle by using a vibratory pressure due to a piezoelectric element can be used in the present invention. The thermal ink jet system can enhance: the accuracy of a diameter of an ejection orifice and the heat quantity of a heat pulse used for ejection in an individual ejection unit for liquid formulation, and the accuracy of a size of a micro heater or the like used therefor; and the reproducibility. Accordingly, the thermal ink jet method can achieve a narrow distribution of the diameters of liquid droplets over the all of many ejection units for a liquid formulation, which are densely arranged on an ejection head. In addition, in a situation in which the present invention is frequently used, the device is required to satisfy demands that a manufacture cost is low, the head must be changed frequently, and the device is small, and then the thermal ink jet system is further preferably used.

The present inventors consider the reason why a compound having a betaine skeleton so greatly contributes to the ejection stability, in the following way. A betaine skeleton has both of a quaternary ammonium cation and an organic acid anion in a near position to each other in one molecule, and has features of: tending to be very easily hydrated; being easily modified by other molecules and being able to have an alkyl group or acyl group of a long chain in the molecule; and therefore tending to show high hydration property even when a compound having the betaine skeleton also has the alkyl group of the long chain. On the other hand, protein and peptide are strongly hydrophobic and are difficult to become stable by hydration. When the compound having a betaine skeleton has a hydrophobic group such as the above-described alkyl group and acyl group with a long chain, these functional group acts on a hydrophobic site in protein or peptide, and at the same time the cation and anion of the betaine skelton hydrate the protein and the peptide by the hydration force of the cation and anion having high hydration property, to stabilize them and inhibit interaction between proteins with each other and between peptides with each other. By the action, the compound having a betaine skeleton can inhibit the protein and the peptide from causing denaturation and aggregation due to an energy load when the liquid is ejected based on the principle of the thermal ink jet method, and can stabilize the ejection.

A compound having a betaine skeleton to be used in the present invention has preferably a chemical structure as is represented by the following formula (1).

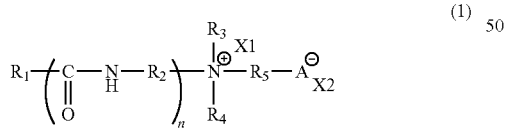

Here, $R_1$ in the formula (1) is a substituted or unsubstituted alkyl group having 6 to 18 carbon atoms, and more preferably a saturated alkyl having 8 to 16 carbon atoms. In the formula (1), $R_2$ and $R_5$ are each independently a substituted or unsubstituted alkylene chain having 1 to 6 carbon atoms, and more preferably and particularly, an alkylene chain having 1 to 4 carbon atoms. In the formula (1), $R_3$ and $R_4$ are each independently an alkyl group or an alkylene chain each having 1 to 6 carbon atoms, and $R_3$ and $R_4$ may be bonded together to form a heterocyclic ring.

An example of the above-described compound includes dimethyldialkylbetaine, diethyldialkylbetaine and methylethyldialkylbetaine; and imidazolium betaine having a heterocyclic ring as well represented by the following formula (2).

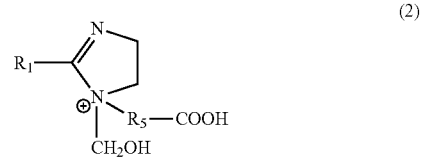

In the formula 1 and the formula 2, A is an anion of an organic acid, and is more preferably a carboxylic group or a sulfonic group. When A is a sulfonic group, $R_5$ has preferably a hydroxyl group.

In the formula (1) and the formula (2), $X_1$ and $X_2$ are counter ions, and $X_1$ has only to be an anionic species, and has only to have at least one selected from inorganic and/or organic anions. An example of the counter ion of $X_1$ preferably includes a halide ion, a chloride ion, a bromide ion, an iodide ion, a fluoride ion, a hydroxide ion, a carboxylic acid ion, a nitric acid ion, a phosphoric acid ion and a sulfuric acid ion; and the counter ions may be the same or different from $X_2$. $X_2$ has only to be a cationic species, and represents at least one selected from a monovalent metal ion, a metal oxide ion and an organic cation. The counter ion of $X_2$ may be the same as or different from $X_1$.

In the formula (1), n is the repetition number of the skeleton, and is 0 or 1. When n is 0, the compound is alkylbetaine shown in the formula (3); and when n is 1, the compound is alkylamide alkylbetaine shown in the formula (4) or the formula (5).

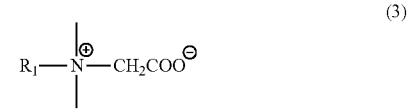

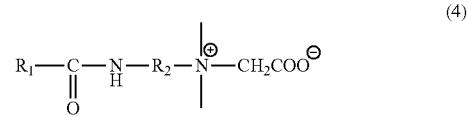

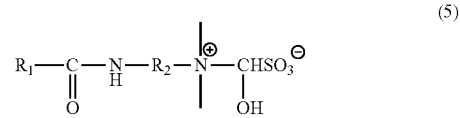

A compound having a betaine skeleton used in the present invention can include alkylamide alkylbetaine, a salt thereof, and a derivative thereof in such a range that the effect of the present invention is not deteriorated, and preferably alkylamide alkylbetaine is used.

The ejection liquid of the present invention is prepared, though being not particularly limited to the following procedure, by mixing a compound having betaine skeleton having surface-active properties and at least one kind of a protein and a peptide with a liquid having a composition composed of a liquid medium mainly containing water and other additive components, which are the above-described components of the ejection liquid. The form of a liquid mixture is not particularly limited, and may be any of a solution type, a suspension type, an emulsion type and a dispersion type. When the liquid mixture is not the solution type, a usable size of a suspended matter, an emulsified matter or a dispersed matter in a medium is in a range of a subnanometer scale to a micrometer scale.

In the present invention, the present inventors have further found that it is possible to keep the stability of ejection even when the concentration of an additive is largely decreased, by adding a surfactant together with a compound having a betaine skeleton. The addition of 0.2 to 1 part by weight of the surfactant with respect to 1 part by weight of a compound having the betaine skeleton can reduce an amount of a compound having the betaine skeleton to be added, with respect to a solution having the same concentration of protein, into 1/10 to 1/2 while keeping the stability of the ejection.

The effect of a surfactant is considered to be different from effect of a compound having a betaine skeleton, and to stabilize ejection through the action of inhibiting the denaturation of protein and the action of redissolving protein which has once aggregated. It is considered that the combination of these two different effects develops a synergistic effect to greatly improve the stabilization of ejection. It is considered that the single addition of a surfactant could not completely inhibit the aggregation of protein because the surfactant alone has no large effect, whereby it could not secure the stability of ejection.

A surfactant of the present invention means a compound which has both of a polar part and a nonpolar part in one molecule, has each of the above-described parts in a distant region from each other in the molecule, and has a property capable of reducing an interfacial tension between two immiscible phases by alignment of the molecular of the surfactant between the two immiscible phases and capable of forming a micell.

Examples of the surfactant that can be used typically includes, but is not limited to, sorbitan fatty acid esters such as sorbitan monocaprylate, sorbitan monolaurate and sorbitan monopalmitate; glycerin fatty acid esters such as glycerin monocaprylate, glycerin monomyristate and glycerin monostearate; polyglyceryl fatty acid esters such as decaglyceryl monostearate, decaglyceryl distearate and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate and polyoxyethylene sorbitan tristearate; polyoxyethylene sorbitan fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ethers; polyoxyethylene polyoxypropylene alkyl ethers such as polyoxyethylene polyoxypropylene glycol ether, polyoxyethylene polyoxypropylene propyl ether and polyoxyethylene polyoxypropylene cetyl ether; polyoxyethylene alkyl phenyl ethers such as polyoxyethylene nonylphenyl ether, polyoxyethylene hydrogenated castor oils such as polyoxyethylene castor oil and polyoxyethylene hydrogenated castor oil (polyoxyethylene hydrogen castor oil); polyoxyethylene beeswax derivatives such as polyoxyethylene sorbit beeswax; polyoxyethylene lanolin derivatives such as polyoxyethylene lanolin; polyoxyethylene stearic acid amides having HLB of 6 to 18 out of polyoxyethylene fatty acid amides; anionic surfactants including alkyl sulfate containing an alkyl group having 8 to 18 carbon atoms such as sodium cetyl sulfate, sodium lauryl sulfate and sodium oleyl sulfate, and polyoxyethylene alkyl ether sulfates containing 2 to 4 moles by average of ethyleneoxide added and an alkyl group having 8 to 18 carbon atoms such as polyoxyethylene sodium lauryl sulfate; an alkylbenzene sulfonates containing an alkyl group having 8 to 18 carbon atoms such as sodium lauryl benzenesulfonate; alkyl sulfosuccinates containing an alkyl group having 8 to 18 carbon atoms such as sodium lauryl sulfosuccinate; natural surfactants such as lecithin and glycerophospholipid; sphingophospholipids such as sphingomyelin; and saccharose fatty acid esters of a fatty acid having 8 to 18 carbon atoms. An ejection liquid (liquid composition) of the present invention can contain one or more of these surfactants in combination.

The surfactant is preferably polyoxyethylene sorbitan fatty acid ester, is particularly preferably polyoxyethylene 20 sorbitan monolaurate, polyoxyethylene (4) sorbitan monooleate, polyoxyethylene 20 sorbitan monopalmitate, polyoxyethylene 20 sorbitan monostearate, polyoxyethylene 20 sorbitan tristearate, polyoxyethylene 20 sorbitan monolaurate, polyoxyethylene (5) sorbitan monooleate and polyoxyethylene 20 sorbitan tri-oleate, and is most preferably polyoxyethylene 20 sorbitan monolaurate and polyoxyethylene 20 sorbitan monooleate. In addition, the surfactant particularly preferable for lung inhalation is polyoxyethylene 20 sorbitan monolaurate and polyoxyethylene 20 sorbitan monooleate.

A concentration of a surfactant to be added can be, for instance, 0.001 to 20% by weight in the case of insulin, though depending on coexisting protein or the like. The content of a surfactant to be added is preferably 0.2 to 10 parts by weight, with respect to 1 part by weight of a compound having a betaine skeleton.

In an embodiment of the present invention, an antibacterial agent, a disinfectant and an antiseptic agent may be added in order to eliminate the influence of a microorganism. A compound having a betaine skeleton to be used in the present invention has the above-described effect, but the agent having the effect further includes, for instance, a quaternary ammonium salt such as benzalkonium chloride and benzathonium chloride; a phenol derivative such as phenol, cresol and anisole; benzoic acids such as benzoic acid and p-hydroxybenzoate ester; and sorbic acid.

In an embodiment of the present invention, an ejection liquid may include oil, glycerin, ethanol, urea, cellulose, polyethylene glycol and alginate, so as to increase the physical stability for cohesion and precipitation occurring while being preserved; and may include ascorbic acid, citric acid, cyclodextrin, tocopherol and other antioxidantal agents, so as to increase the chemical stability for preventing deterioration and oxidation.

An ejection liquid may include a buffer agent for adjusting pH. A usable buffer solution includes, for instance, ascorbic acid, citric acid, diluted hydrochloric acid, diluted sodium hydroxide, further sodium hydrogenphosphate, sodium dihydrogenphosphate, potassium hydrogenphosphate, potassium dihydrogenphosphate, PBS, Hepes and Tris.

An ejection liquid may include an isotonizing agent such as aminoethyl sulfonic acid, potassium chloride, sodium chloride, glycerin and sodium hydrogen carbonate.

An ejection liquid may include a corrigent for taste and smell such as saccharide like glucose and sorbitol, a sweetening agent like astel palm, menthol and various flavors. In addition, the usable corrigent may be not only a hydrophilic compound, but also a hydrophobic compound or an oily compound.

When the ejection liquid of the present invention is used for preparing a biochip and a biosensor or screening protein, a system which is approximately similar to a currently commercially available ink jet printer can be used.

Figure 2:
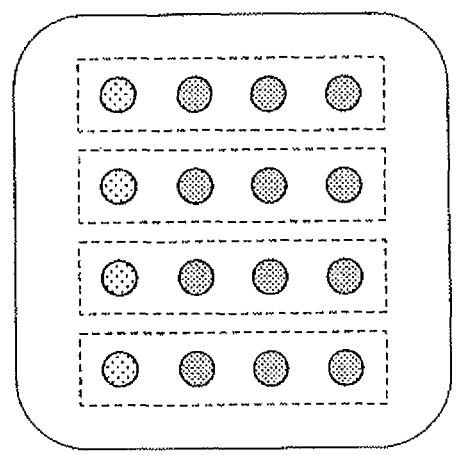
FIG. 2 is a view for showing one example of a pattern of protein arranged on a substrate.

A method of ejecting protein with the use of the ejection liquid of the present invention will be now described in detail with reference to FIG. 1. A pattern is formed by the steps of: filling the ejection liquid into a nozzle of an ink jet head 3 from a tank 1; and making the ink jet head eject the ejection liquid onto a substrate 5 suitable for each purpose, by driving the ink jet head while keeping a fixed space between the substrate and the nozzle face of the ink jet head. In FIG. 1, reference numeral 2 denotes a liquid flow path, reference numeral 4 denotes liquid droplets, and reference numeral 6 denotes a drive controller. It is recommended to use a drive controller when ejecting the ejection liquid so as to form the pattern according to an image pattern on the substrate, and it is preferable to form such a pattern that spots are not connected with each other as shown in FIG. 2.

An ejection liquid in the present invention can include various additives adaptable to a purpose of an application of an atomisation liquid, for instance, a proper amount of a surface moderator, a viscosity modifier, a solvent and a moisturizing agent, as needed.

Specifically, a blendable additive includes, for instance, a hydrophilic binder, a hydrophobic binder, a hydrophilic thickener, a hydrophobic thickener, glycol derivatives, alcohols, a corrigent for taste, a corrigent for smell and an electrolyte, which may be a single substance or a mixture selected from them.

Here, various substances to be used for the above exemplified additives are more preferably permitted to use in a medicinal use described in a pharmacopoeia of each country as a secondary component which may be added when preparing a liquid formulation for therapy, or in a food product and a cosmetic article.

Various substances to be blended as the above-described additive are preferably added generally each in a range of 0.01 to 40% by a weight ratio, and more preferably in a range of 0.1 to 20%, though the value depends on a type of objective protein and peptide. In addition, an amount of the above-described additive to be added is preferably 0.5 to 200 parts by weight with respect to 1 part by weight of the above-described protein and peptide from a viewpoint of an ejection property, though the amount varies with a type, amount and combination of the additives.

An atomiser of the present invention has preferably a structure having an ejection head part which can eject a liquid fine droplet of the liquid formulation while applying thermal energy to the liquid formulation and works based on a thermal ink jet principle, and many ejection units for the liquid formulation, which compose the head part and can be independently driven. Furthermore, the atomiser preferably has a form provided with: an electrical connection part used for connecting a plurality of control signals required for independently driving each of the ejection units for the liquid formulation, integrated with a wire for connecting the ejection units for the liquid formulation with each other; in addition, a tank for accommodating the above-described liquid formulation; and an integrally composed cartridge for nebulizing a liquid while including a liquid flow path, as means for supplying the liquid formulation from the tank to the ejection head based on the thermal ink jet principle.

FIG. 3 diagrammatically shows an example of the whole configuration of such a cartridge for nebulizing a liquid. The cartridge illustrated in FIG. 3 is produced by arranging a head part 9 for nebulizing a liquid formulation, a tank 7 for filling the liquid formulation therein, and a liquid flow path 8 for introducing the liquid formulation from the tank 7 to the head part 9, integrally on the same substrate. A controller for controlling the driving of each ejection unit for a liquid formulation in the head part 9 exchanges a driving signal, a control signal and the like with the head part 9, through an electrical connection part 11 to which an inner wire 10 is connected.

In the above arrangement, a head part 9 preferably employs the head for ejecting a liquid ultrafine droplet, which ejects liquid droplets in an individual liquid amount of a subpicoliter or femtoliter order, has superior controllability for the liquid amount and is disclosed in Japanese Patent Application Laid-Open No. 2003-154655.

In examples shown in FIG. 1 and FIG. 3, one type of a liquid formulation is atomised, so that there is one tank for filling the liquid formulation therein in the structure. When two or more types of liquid formulations are atomised, it is possible to cope with the case by arranging a plurality of tanks for filling the liquid formulations appropriately corresponding to them, and making a thermal ink jet head have a configuration of having integrated a plurality of ejection units for the liquid formulations.

When ejecting the ejection liquid of the present invention onto a substrate with the use of the ink jet system, it is also possible to efficiently react the substrate with a substance to be detected, by ejecting a solution containing the substance to be detected onto the substrate in the same pattern, and to change the concentration of protein by only changing an amount to be ejected. Accordingly, the atomiser can be used for preparing a biochip, a biosensor, and a device for sensing and screening a biological substance. Furthermore, the atomiser is effectively used through employing a head capable of ejecting the above-described liquid fine droplet, when it is required to use the above-described extremely microdroplet as an individual liquid droplet to be ejected, for instance, when a somatic cell with a size of several micrometers has to be applied as a drug.

An inhalation device of the present invention makes use of an advantage peculiar to the form in the inhalation device, which separates a process of transforming a liquid formulation to a liquid fine droplet from a process of mixing the atomised liquid fine droplet into an airflow for transporting the liquid fine droplet, which is a feature of a nebulizing method of the present invention. When nebulizing a liquid formulation containing an ejection liquid (liquid composition) in a predetermined concentration, which is specified in the present invention and can be used for a therapeutic purpose, into an airflow, and when making a person to be administered inhale the atomised liquid formulation, the inhalation device can arbitrarily set an amount of a drug compound (dose per single dosage) in the liquid composition contained in a gas to be inhaled, which can be used for the therapeutic purpose. The inhalation device to be used for the above purpose can be miniaturized so that a user can carry and hold it, by using an ejection head based on the thermal ink jet principle, which arranges openings for ejecting liquid fine droplets therein at high density per unit area, as a nebulizing mechanism for nebulizing the above-described liquid formulation.

In the inhalation device which uses the above-described ejection liquid for lung inhalation, an essential part is a device which can eject a formulated substance of the present invention in a form of liquid droplets with particle sizes of 1 to 5 μm and with a narrow distribution. A head part for ejecting the liquid droplet is a removable cartridge unit which was described in the above with reference to FIG. 3.

An inhalation device as a controller for ejection is composed so that a user can carry and hold, and an inhaler can make a user inhale a drug in a form of liquid droplets which are ejected so as to acquire a uniform particle size and a constant amount.

An outline of an example for an inhaler usable in the present invention will be now described with reference to FIG. 4 and FIG. 5.

Figure 4:
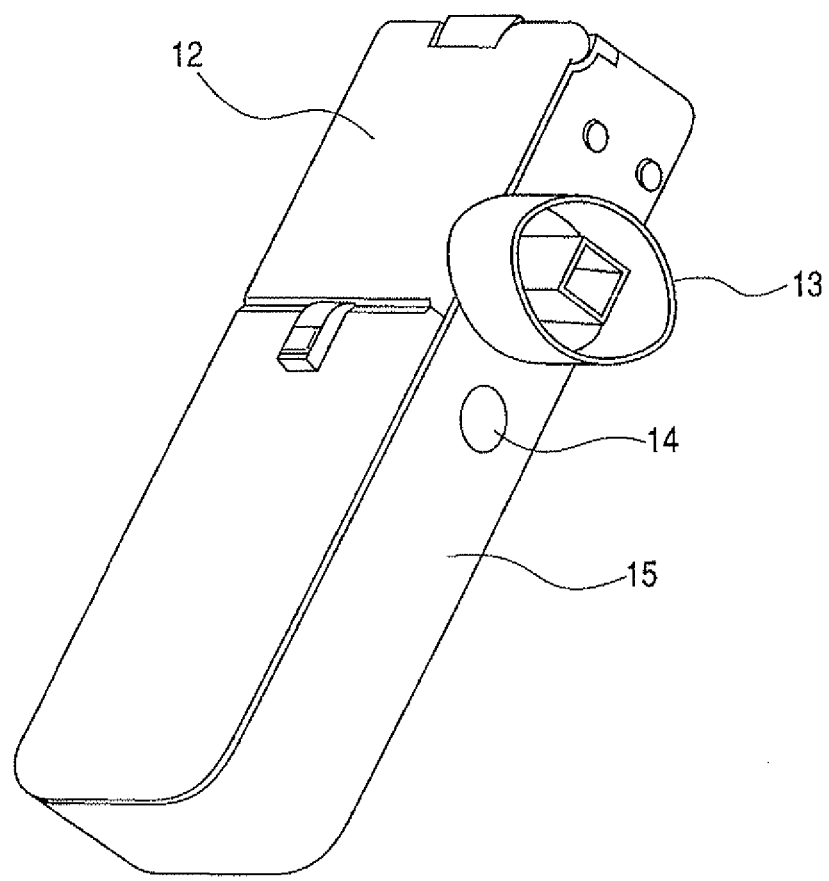
FIG. 4 is a perspective view of an inhaler.

FIG. 4 is a perspective view showing an appearance of an inhaler, reference numeral 15 denotes a main body of the inhaler, and reference numeral 12 denotes an access cover, both of which form a housing. Reference numeral 14 denotes a power button. FIG. 5 illustrates a state in which the access cover 12 is opened. When the access cover 12 is opened, a head cartridge unit 16 and a mouthpiece 13 appear. When a user starts an inhalation operation, air flows into a mouthpiece 13 from an air intake, is mixed with a drug ejected from an ejection opening provided in a head part 9 of the head cartridge unit 16 to form a fluid mixture, and flows to an outlet of the mouthpiece which has a shape to be taken in a mouth of a human. The user can effectively inspire a drug solution ejected as liquid droplets from a liquid-ejecting part of a head cartridge unit, through inserting a tip of the mouthpiece inside the mouth, holding it with a tooth, and inhaling air.

In other words, a configuration of the intake part corresponds to an inhalation mechanism for making a person to be administered inhale a gas in which liquid fine droplets of a liquid formulation produced by a nebulizing mechanism float in a mist form.

Figure 3:
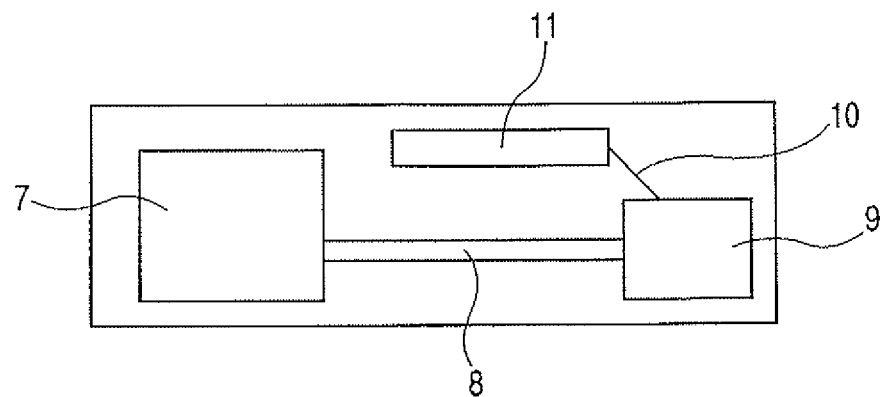
FIG. 3 is a diagrammatic explanatory drawing of a head cartridge unit for an inhaler.
Figure 5:
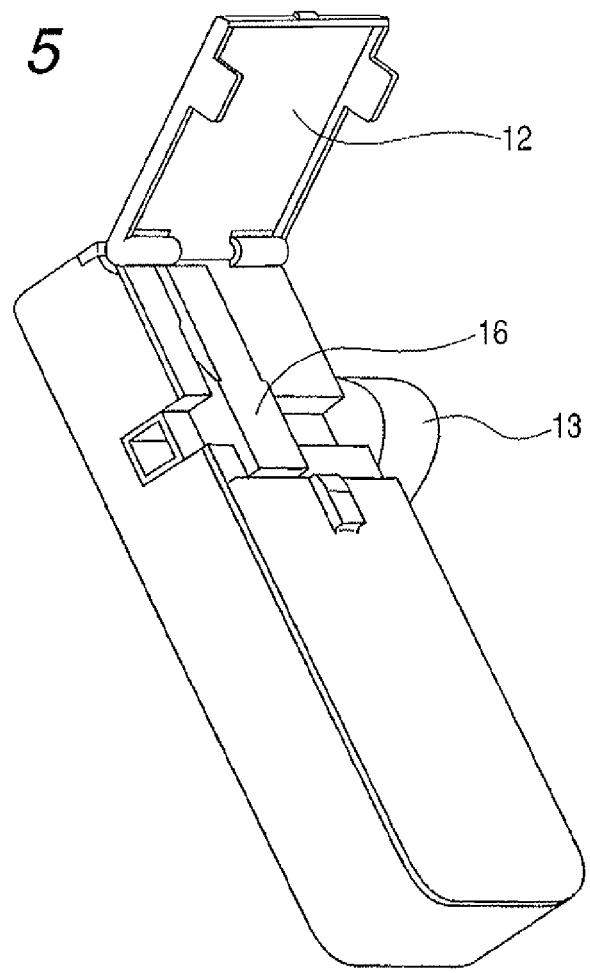
FIG. 5 is a perspective view for a state in which an access cover is opened in FIG. 4.
Figure 6:
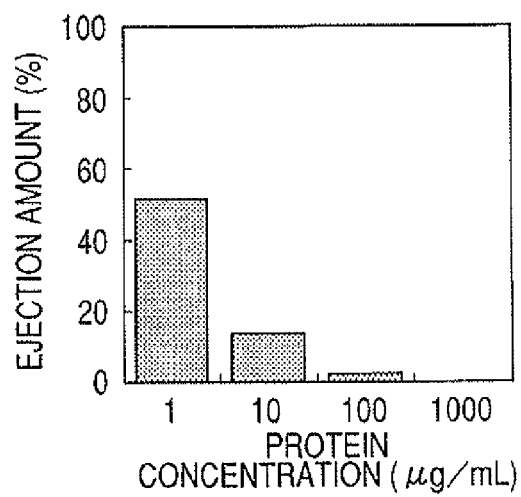
FIG. 6 is a graph showing an ejection rate when an albumin solution is ejected with the thermal ink jet system.

FIG. 4 and FIG. 5 show a configuration of an example of an inhaler to be used for a medical purpose, which is miniaturized so that a user can carry and hold it. A main body of the inhaler 15 consists of a housing for accommodating a cartridge for nebulizing liquid, a controller thereof and a power source (battery); and a mouthpiece 13 to cover a mouth when inhaling air, mounted thereon. The cartridge for nebulizing liquid is integrated with a tank for a liquid formulation as is illustrated in FIG. 3, and has such a configuration that it can be exchanged after an access cover 12 has been opened. FIG. 5 illustrates a state in which the access cover 12 is opened. A head cartridge unit 16 is installed on some midpoint of a tubular airflow path for introducing air which flows in from an air intake opening, to a mouthpiece 8 therethrough. A head part of the head cartridge unit 16 converts a liquid formulation into liquid fine droplets based on the principle of the thermal ink jet system, and the tubular airflow path mixes them in airflow therein, and atomises them. The inhaler employs a system of introducing air inside it from the air intake opening, when a user takes the mouthpiece 13 in a mouth and inhales air through the mouthpiece.

By adopting a configuration shown in FIG. 5, the inhaler achieves a form which can naturally make atomised liquid fine droplets of a liquid formulation arrive at a fauces and inside the trachea of a person to be administered, together with inspired air. Accordingly, an amount (dose) of the liquid formulation to be atomised does not depend on varying volumes of the inspired air, and is independently controlled. Specifically, a head part of a head cartridge unit 16 employs a head for ejecting the liquid ultrafine droplet disclosed in Japanese Patent Application Laid-Open No. 2003-154655, and has a configuration of controlling the diameter of the droplets to about 3 μm by average.

EXAMPLES

First of all, in order to further promote understanding for difficulty in the ejection of a protein solution, an ejected amount of protein when only protein has been ejected with the thermal ink jet system will be shown. A protein solution was prepared by dissolving albumin in PBS, and the solution of each concentration was ejected by using a thermal ink jet printer (trade name: PIXUS950i, manufactured by Canon Inc.) which has been remodeled so that the ejected solution can be recovered. The amount of ejected each albumin solution was expressed by values with respect to 100% of the ejected amount of pure water which has been ejected in the same manner. The results are shown in FIG. 6.

It is understood that a solution containing albumin even as in a low concentration as 1 μg/mL is not completely stably ejected, and as a solution contains more protein, it is slowly hardly ejected. When carrying out such as operation as is required in the present invention, liquid droplets with a smaller diameter has to be ejected, and it is conceivable that a protein solution is hardly ejected.

The present invention will be now described in further detail with reference to the following Examples, but Examples are specific examples shown for deeper understanding, and the present invention is not limited to these specific examples at all. Hereafter, "%" means % by weight.

Examples 1 to 12 and Comparative Examples 1 to 13

(Confirmation of Diameter of Atomised Particle)

An aqueous solution containing 30% of ethanol was filled in a head cartridge having a nozzle diameter of 3 μm to be used in an ejection experiment, and a size and size distribution of the ejected particles were confirmed by measuring them with the use of a laser-diffraction-type particle size distribution measuring instrument (Spraytec manufactured by Malvern Instruments Ltd.). As a result, it was detected that the ejected particles are certainly liquid droplets having a sharp particle size distribution at 3 μm.

(Liquid Droplet Formation from Protein Solution Based on Principle of Thermal Ink Jet System)

An ejection liquid was prepared by the steps of: previously dissolving an appropriate concentration of albumin in purified water; further adding a compound having a betaine skeleton while stirring the solution; and then quantitatively determining the volume with purified water so that the concentration of each substance can have its desired concentration.

A prepared ejection liquid was ejected by the steps of: filling the ejection liquid in the above-described head cartridge having the nozzle diameter of 3 μm; connecting the head cartridge with an ejection controller; setting the frequency to 20 kHz and the voltage to 12 V; ejecting the ejection liquid for one second; and again ejecting it after the interval of 3 seconds. The ejection liquid was ejected based on the principle of the thermal ink jet system. The ejection operation was repeated for 50 times and it was visually confirmed whether the ejection liquid was ejected, or not. The ejection liquid which was ejected for 50 operations was evaluated as "○", the ejection liquid of 15 to 49 operations as "Δ", and the ejection liquid of less than 15 operations as "×". In addition, the atomised ejection liquid was recovered, and it was confirmed whether the composition changed or not, by analyzing the ejection liquids before and after ejection, through an HPLC analysis (in a measurement condition of apparatus: JASCO Corporation; column: YMC-Pack Diol-200, 500×8.0 mm ID; eluent: a liquid including 0.1M $KH_2PO_4$—$K_2HPO_4$(pH 7.0) 0.2M NaCl; flow rate: 0.7 mL/minute; temperature: 25° C.; detection: UV 215 nm). An ejection test shown below was carried out in the above-described conditions, with the use of a head cartridge having the above-described nozzle with the diameter of 3 μm and an ejection controller.

As a comparative example, an ejection liquid was prepared which contains pure water, various protein solutions and substances having nothing to do with the present invention, and was subjected to an ejection experiment as in the case of the present examples. Formulations and results examined on Examples and Comparative Examples were listed in the following Table 1.

TABLE 1

|  | Protein | | Compound having betaine skeleton | | Surfactant and additive | | Ejection property |
| --- | --- | --- | --- | --- | --- | --- | --- |
|  | Type | Concentration | Type | Concentration | Type | Concentration | Evaluation |
| Example 1 | albumin | 1 mg/ml | lauramidepropyl betaine | 10 mg/ml | none | — | ○ |
| Example 2 | albumin | 1 mg/ml | cocamidepropyl betaine | 10 mg/ml | none | — | ○ |
| Example 3 | insulin | 4 mg/ml | cocamidepropyl betaine | 10 mg/ml | none | — | ○ |
| Example 4 | insulin | 4 mg/ml | lauramidepropyl betaine | 10 mg/ml | none | — | ○ |
| Example 5 | insulin | 4 mg/ml | lauryl betaine | 50 mg/ml | none | — | ○ |
| Example 6 | glucagon | 0.5 mg/ml | cocamidepropyl betaine | 3 mg/ml | none | — | ○ |
| Example 7 | GLP-1 | 1 mg/ml | cocamidepropyl betaine | 10 mg/ml | none | — | ○ |
| Example 8 | hGH | 1 mg/ml | cocamidepropyl betaine | 10 mg/ml | none | — | ○ |
| Example 9 | EPO | 1 mg/ml | lauramidepropyl betaine | 10 mg/ml | none | — | ○ |
| Example 10 | IFN α | 1 mg/ml | lauramidepropyl betaine | 10 mg/ml | none | — | ○ |
| Example 11 | IFN γ | 1 mg/ml | lauramidepropyl betaine | 10 mg/ml | none | — | ○ |
| Example 12 | calcitonin |  | lauramidepropyl betaine | 10 mg/ml | none | — | ○ |
| Comparative Example 1 | water | — | none | — | none | — | ○ |
| Comparative Example 2 | albumin | 1 mg/ml | none | — | none | — | x |
| Comparative Example 3 | insulin | 4 mg/ml | none | — | none | — | x |
| Comparative Example 4 | glucagon | 0.5 mg/ml | none | — | none | — | x |
| Comparative Example 5 | GLP-1 | 1 mg/ml | none | — | none | — | x |
| Comparative Example 6 | hGH | 1 mg/ml | none | — | none | — | x |
| Comparative Example 7 | EPO | 1 mg/ml | none | — | none | — | x |
| Comparative Example 8 | IFN α | 1 mg/ml | none | — | none | — | x |
| Comparative Example 9 | IFN γ | 1 mg/ml | none | — | none | — | x |
| Comparative Example 10 | calcitonin | 1 mg/ml | none | — | none | — | x |
| Comparative Example 11 | albumin | 1 mg/ml | none | — | TWEEN80 | 10 mg/ml | x |
| Comparative Example 12 | insulin | 4 mg/ml | none | — | TWEEN20 | 10 mg/ml | Δ |
| Comparative Example 13 | insulin | 4 mg/ml | none | — | TWEEN20 | 50 mg/ml | x |

Pure water of Comparative Example 1 was stably ejected because of containing no protein, whereas ejection liquids of Comparative Examples 2 to 13, which does not contain a compound having a betaine skeleton, was ejected little or was not ejected at all, regardless of the type of the protein and the presence or absence of an additive. Liquids of Comparative Examples 11 to 13 which contain a surfactant TWEEN were ejected to some extent, but was not sufficiently stably ejected. It is understood that in contrast to this, Examples 1 to 12 are normally and stably ejected. As a result of an HPLC analysis, Examples 1 to 12 did not show a change of a peak location and a peak area before and after ejection, and a change of a liquid composition, either.

Examples 13 and 14

(Effect onto Each Protein, and Concentration of Additive)

Subsequently, lauramidepropyl betaine or cocamidepropyl betaine was selected as a compound having a betaine skeleton and was added to each protein so as to be a predetermined concentration. These ejection liquids were evaluated by the same ejection experiment as in Example 1. Formulations and results examined on the present examples are listed in the following Table 2.

Although the necessary concentration of alkylamide propyl betaine to be added varies with the concentration and type of protein, the addition of alkylamide propyl betaine makes each protein normally ejected on the basis of the principle of the thermal ink jet system, and it was confirmed that alkylamide propyl betaine exerts the effect to a wide range of protein with a small amount. As a result of an HPLC analysis, Examples 13 and 14 did not show a change of a peak chart before and after ejection, and a change of a liquid composition.

Examples 15 to 19

(Synergistic Effect of Compound Having Betaine Skeleton and Surfactant)

A solution was prepared by adding a compound having a betaine skeleton into protein, and an ejection liquid was prepared by further adding a surfactant to the solution. These ejection liquids were evaluated by the same ejection experiment as in Example 1. Formulations and results examined on the present examples are listed in the following Table 3.

TABLE 2

|  | Protein | | Compound having betaine skeleton | | Surfactant and additive | | Ejection property |
| --- | --- | --- | --- | --- | --- | --- | --- |
|  | Type | Concentration | Type | Concentration | Type | Concentration | Evaluation |
| Example 13 | insulin | 4 mg/ml | cocamidepropyl betaine | 3 mg/ml | none | — | ○ |
| Example 14 | insulin | 4 mg/ml | lauramidepropyl betaine | 3 mg/ml | none | — | ○ |
| Comparative Example 14 | insulin | 4 mg/ml | none | — | TWEEN20 | 3 mg/ml | x |

TABLE 3

| | Protein | | Compound having betaine skeleton | | Surfactant and additive | | Ejection property |
|---|---|---|---|---|---|---|---|
| | Type | Concentration | Type | Concentration | Type | Concentration | Evaluation |
| Example 15 | insulin | 4 mg/ml | lauryl betaine | 2 mg/ml | TWEEN20 | 0.5 mg/ml | ○ |
| Example 16 | albumin | 1 mg/ml | lauramidepropyl betaine | 5 mg/ml | TWEEN80 | 5 mg/ml | ○ |
| Example 17 | albumin | 1 mg/ml | cocamidepropyl betaine | 5 mg/ml | TWEEN80 | 5 mg/ml | ○ |
| Example 18 | albumin | 1 mg/ml | lauramidepropyl betaine | 3 mg/ml | TWEEN80 | 2 mg/ml | ○ |
| Example 19 | albumin | 1 mg/ml | cocamidepropyl betaine | 3 mg/ml | TWEEN80 | 2 mg/ml | ○ |

A protein solution simultaneously containing alkylamide propyl betaine and TWEEN as an additive could be ejected, even when the concentration of a compound having a betaine skeleton is extremely low in comparison with the case when the compound having a betaine skeleton was singly added. In addition, a protein solution could be ejected even when containing such a concentration of a compound having a betaine skeleton as did not make the protein solution ejected, which singly contains the same amount of it. As a result, a total amount of an additive can be greatly reduced. As a result of an HPLC analysis, Examples 15 to 19 did not show a change of a peak chart before and after ejection, and a change of a liquid composition.

Example 20

(Preparation of Antibody Chip with Use of an Ink Jet Printer, and Sensing)

Figure 7:
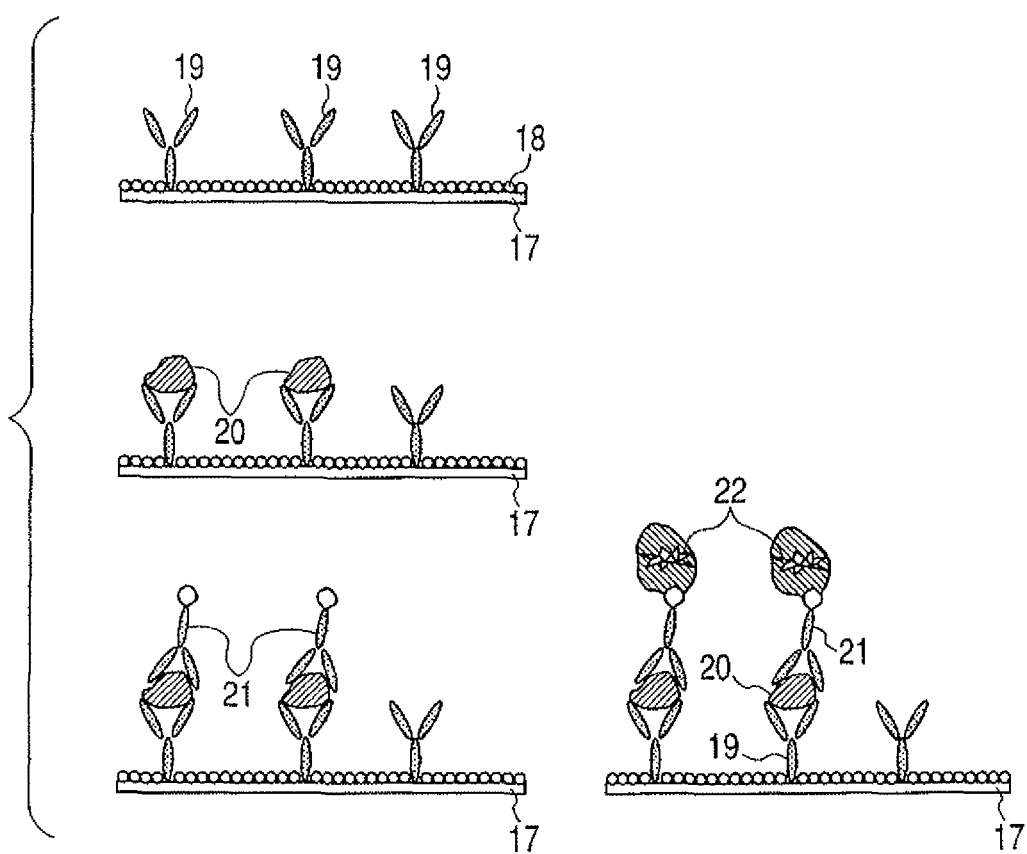
FIG. 7 is a model view of an experimental procedure in Example 20.

A Human IL2 monoclonal antibody, a Human IL4 monoclonal antibody and a Human IL6 monoclonal antibody were prepared into a liquid having a concentration of 0.1 to 500 μg/mL, respectively. Each ejection liquid was prepared by adding lauramidepropyl betaine into the liquid so that the concentration of the betaine is 1% (w/w). The ejection liquid was filled in the head of an ink jet printer (trade name: PIXUS950i, manufactured by Canon Inc.), and was ejected onto a Poly-L-Lysin-coated slide glass. FIG. 7 shows a model view of the present example. In the figure, reference numeral 17 denotes a substrate, reference numeral 18 denotes a masking reagent, reference numeral 19 denotes a substance (such as protein and peptide) specifically reacting with a substance to be detected, reference numeral 20 denotes a substance to be detected, reference numeral 21 denotes the substance specifically reacting with the substance to be detected, and reference numeral 22 denotes an indicator.

The antibody which had been ejected onto a glass was incubated at 4° C., and the glass on which the antibody was incubated was masked with 1% BSA. The glass was carefully cleaned after having had been masked, and was supplied as an antibody chip substrate. Subsequently, a solution which contains 1 μg/mL each of recombinants IL2, IL4 and IL6 that were substances to be detected by the chip was prepared together with 1.0% lauramidepropyl betaine (w/w), 0.5% TWEEN20 (w/w) and 0.1% BSA (w/w). The liquid was filled in the head of an ink jet printer (trade name: PIXUS950i, manufactured by Canon Inc.), and was ejected on the above-described substrate so as to form the same pattern. After the liquid was ejected, the substrate was covered with a cover glass, and was subjected to the reaction at 4° C. After the reaction, the substrate was carefully cleaned and dried.

Subsequently, a substrate specifically bonded with a sample was reacted with a substrate, and the substance was indicated. A solution containing a substance specifically bonded with the sample was prepared by blending each 1 μg/mL biotin-indicated antibody liquid (biotinylated Human IL2 monoclonal antibody, biotinylated Human IL4 monoclonal antibody and biotinylated Human IL6 monoclonal antibody), 1.0% lauramidepropyl betaine (w/w), 0.5% TWEEN20 (w/w) and 0.1% BSA (w/w) so that each component can be its final concentration; was filled in the head of an ink jet printer (trade name: PIXUS950i, manufactured by Canon Inc.); and was ejected onto the above-described substrate so as to form the same pattern. After the liquid was ejected, the substrate was covered with a cover glass, and was subjected to the reaction at 4° C. After the reaction, the substrate was carefully cleaned and dried.

A solution for indication was prepared by blending 10 μg/ml, Cy3 labeling streptavidin, 1.0% lauramidepropyl betaine (w/w), 0.5% TWEEN20 (w/w) and 0.1% BSA (w/w) so that each component can be the final concentration; then was filled in the head of an ink jet printer (trade name: PIXUS950i, manufactured by Canon Inc.); and was ejected onto the above-described substrate so as to form the same pattern. After the liquid was ejected, the substrate was covered with a cover glass, and was subjected to the reaction at 4° C. After the reaction, the substrate was carefully cleaned and dried.

Subsequently, a substrate on which the reaction has been finished was irradiated with excited light, and a quantity of fluorescent signal of light emitted from Cy3 was measured by using a fluorescence scanner having a filter for a transmitted wavelength of 532 nm arranged therein. As the measured result, a fluorescent signal corresponding to the type and concentration of a sample could be detected.

The present invention is not limited to the above embodiments and various changes and modifications are possible within the spirit and scope of the present invention. Therefore to apprise the public of the scope of the present invention, the following claims are made.

This application claims priority from Japanese Patent Application No. 2005-098749 filed on Mar. 30, 2005, which is hereby incorporated by reference herein.

The invention claimed is:

1. An ejection method using an ejection device having: an ejection head based on the principle of a thermal ink jet system for ejecting a liquid; a tank for accommodating the liquid; and a flow path for guiding the liquid accommodated in the tank to the ejection head, comprising:
   supplying the liquid accommodated in the tank from the tank to the ejection head through the flow path;
   applying thermal energy to the supplied liquid; and ejecting the liquid from the ejection head,
wherein the liquid comprises:
lauryl betaine;
insulin in a concentration of no more than 2/25 times a concentration of the lauryl betaine; and
a liquid medium mainly composed of water.

2. An ejection method using an ejection device having: an ejection head based on the principle of a thermal ink jet system for ejecting a liquid; a tank for accommodating the liquid; and a flow path for guiding the liquid accommodated in the tank to the ejection head, comprising:

supplying the liquid accommodated in the tank from the tank to the ejection head through the flow path;
applying thermal energy to the supplied liquid; and
ejecting the liquid from the ejection head,
wherein the liquid comprises:
lauryl betaine;
insulin in a concentration of no more than 2 times a concentration of the lauryl betaine;
polyoxyethylene sorbitan fatty acid ester in a concentration of more than 1/4 times a concentration of the lauryl betaine; and
a liquid medium mainly composed of water.

* * * * *